(12) United States Patent
Hilpert

(10) Patent No.: US 8,763,287 B2
(45) Date of Patent: Jul. 1, 2014

(54) DEVICE FOR SAMPLING BIOLOGICAL TISSUE FOR THE IDENTIFICATION OF ANIMALS

(75) Inventor: Jean-Jacques Hilpert, Vitre (FR)

(73) Assignee: Allflex Europe SAS, Vitre (FR)

( * ) Notice: Subject to any disclaimer, the term of this patent is extended or adjusted under 35 U.S.C. 154(b) by 1023 days.

(21) Appl. No.: 12/444,529

(22) PCT Filed: Oct. 1, 2007

(86) PCT No.: PCT/EP2007/060353
§ 371 (c)(1),
(2), (4) Date: Jun. 10, 2009

(87) PCT Pub. No.: WO2008/040692
PCT Pub. Date: Apr. 10, 2008

(65) Prior Publication Data
US 2010/0016758 A1    Jan. 21, 2010

(30) Foreign Application Priority Data

Oct. 6, 2006  (FR) ...................................... 06 08800

(51) Int. Cl.
*G09F 3/00* (2006.01)
*A01K 29/00* (2006.01)
*A61B 10/00* (2006.01)
*A61B 17/00* (2006.01)
*A61D 1/04* (2006.01)

(52) U.S. Cl.
USPC ................. 40/301; 40/300; 40/302; 119/655; 600/562; 600/564; 600/567; 606/116; 606/117

(58) Field of Classification Search
USPC .................. 600/562, 564, 567; 606/116, 117; 119/655, 814, 858; 40/301
See application file for complete search history.

(56) References Cited

U.S. PATENT DOCUMENTS 2,617,359 A * 11/1952 Van Horn et al. ............. 102/512
6,659,338 B1   12/2003 Dittmann et al.
(Continued)

FOREIGN PATENT DOCUMENTS

DE   298 24 186   8/2000
EP   0 177 201    4/1986
(Continued)

OTHER PUBLICATIONS

International Search Report dated Feb. 14, 2008, from corresponding PCT application.

*Primary Examiner* — Sean Dougherty
*Assistant Examiner* — Devin Henson
(74) *Attorney, Agent, or Firm* — Young & Thompson

(57) ABSTRACT

A device for sampling biological tissue (1) to be used in a label for marking animals includes: a hollow needle (3) having a cutting edge (36) at one end, capable of sampling a biological tissue sample when the sampling device is inserted into the biological tissue; a fixation part (22) of the hollow needle, made as a single piece and including a tank (2) containing a chemical for processing a biological tissue sample, the base of the tank including a partition (211) that is punctured by the needle when a pressure is applied upon the insertion of the sampling device into the biological tissue. After puncturing the partition, the content of the tank flow into the hollow needle and contacts the recovered sample. The end of the hollow needle containing the sample can further be protected by a cap, and the sample remains easily accessible for further analysis.

24 Claims, 3 Drawing Sheets

(56) References Cited

U.S. PATENT DOCUMENTS

Figure 1:
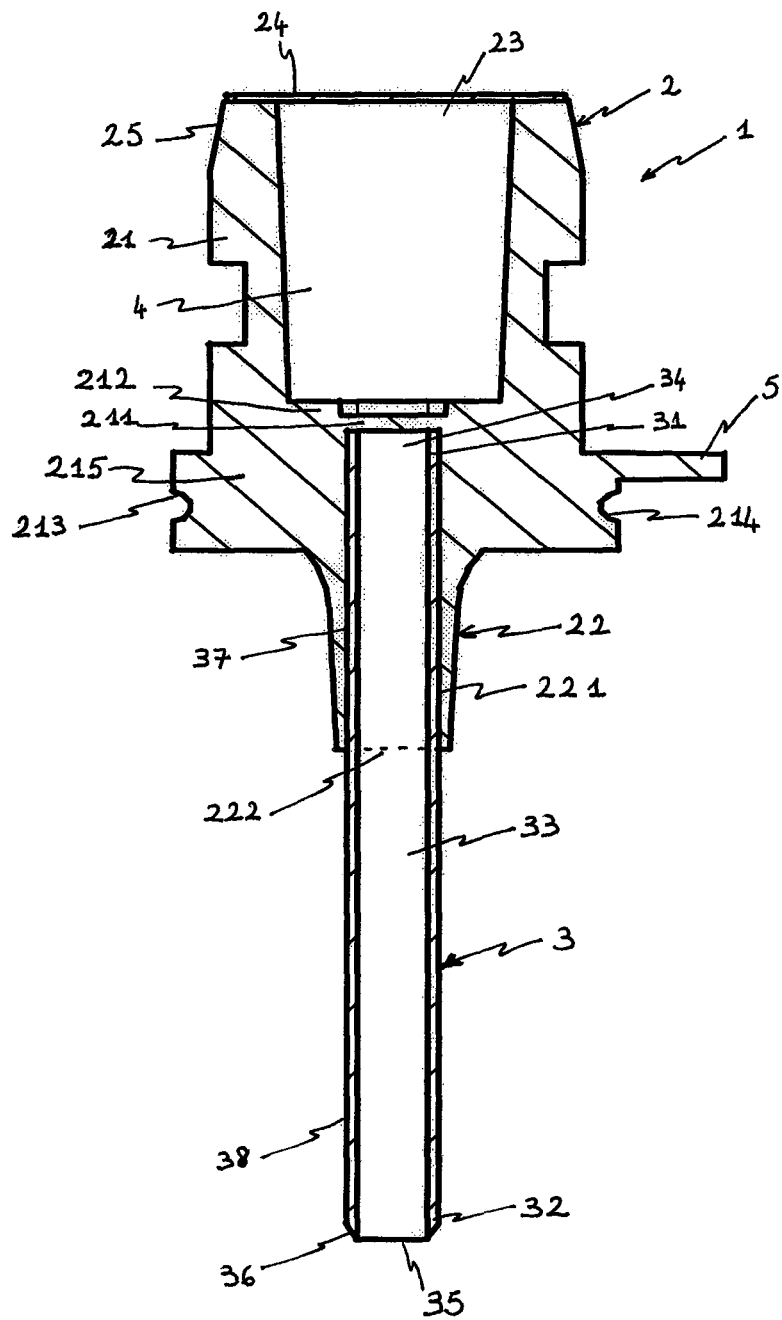

| | | | |
|---|---|---|---|
| 6,968,639 B2 * | 11/2005 | Destoumieux | 40/301 |
| 7,198,629 B2 * | 4/2007 | Brem | 606/116 |
| 7,235,055 B2 * | 6/2007 | Pfistershammer | 600/567 |
| 2008/0044313 A1 * | 2/2008 | Caisley | 422/102 |

FOREIGN PATENT DOCUMENTS

| | | |
|---|---|---|
| EP | 0 913 081 | 5/1999 |
| EP | 1 088 212 | 11/2001 |
| EP | 1 037 525 | 4/2003 |
| EP | 1 014 861 | 3/2004 |
| EP | 1 372 379 | 7/2004 |
| GB | 2 223 409 | 4/1990 |
| WO | 95/25426 | 9/1995 |
| WO | 99/61882 | 12/1999 |
| WO | 02/080661 | 10/2002 |
| WO | 2004/010773 | 2/2004 |
| WO | 2006/000869 | 1/2006 |

* cited by examiner

DEVICE FOR SAMPLING BIOLOGICAL TISSUE FOR THE IDENTIFICATION OF ANIMALS

This invention belongs to the field of tagging and identifying farm animals.

It relates to a device for sampling biological tissue that is designed to be used in a tag for tagging animals, the male part of the tag for tagging animals including the device for sampling biological tissue. The invention also has as its object an ear tag whose male part comprises such a device.

In recent years, the tagging of hoofed livestock such as cattle, swine or sheep has become obligatory in a good number of countries throughout the world. This tagging is generally carried out by applying a tag on one or on both ears of the animal, whereby said tag carries means of identification that make possible the individual identification of each animal. There are numerous versions of tags, all of them comprising a female or receiving part and a male or piercing part. For the placement of such a tag, the animal's ear is positioned between the male part and the female part and, using a pair of pliers, the two parts are connected to one another by punching through the ear. Once placed, the tag is supposed to be impossible to remove, thus preventing any fraud. For this purpose, a certain number of locking mechanisms have been designed that make it possible to keep the male part in the female part once the two parts have been assembled on the animal's ear.

The patents EP 0177201, EP 0913081, WO 95/25426 and EP 1037525 describe the locking mechanisms in the form of a ring, slots and/or an attachment clip that lock the male part in the female part after the tag is assembled.

In addition, it is becoming increasingly important not only to be able to identify an animal with its corresponding tag but also to be able to take a sample of biological tissue from the animal that is thus tagged with the tag, and, during a subsequent stage, to be able to attribute this sample, from which a certain number of biological/biochemical characteristics have been determined, to the animal in question.

The patent EP 1014861 describes a device for taking a biological sample that comprises a test capsule with a receptacle for the sample and a cover for the capsule. The receptacle for the sample and the cover of the capsule form a tag that is applied at the same time that the capsule that contains the sample is prepared and closed. The thus obtained capsule carries the same tag information as the tag that was applied, but it can be separated from it. The sample that is contained in the capsule can therefore be brought to a laboratory to carry out the tests that are necessary for determining a disease or the immunological capacities of the animal.

The patent EP 1088212 describes a device for obtaining and preparing a sample of biological tissue for a molecular genetic diagnosis. The device has a receptacle for receiving the sample and a means for taking the sample, which penetrates the receptacle after the sample is taken and seals it hermetically. In the receptacle for receiving the sample, there is a means for protection against the enzymes that degrade DNA. The sample-collecting means passes through the animal's ear by pressure and penetrates the receptacle for recovering the sample, which is itself associated with a tag that comprises a pointed plate and a perforated plate. The receptacle for recovering the sample is connected in a detachable manner to the perforated plate and can consequently be withdrawn after the sample is taken whereas the tag remains in the animal's ear.

The patent EP 1372379 describes a tag for tagging animals that have a device for sampling organic substance. In this tag, the male part is configured in two elements that can be separated. The first of these two elements remains in the female part of the tag once the tag has been applied, whereas the other element is used to take a sample of organic substance and can move from the front to the rear in the first element.

The drawback of the patents EP 1014861 and EP 1088212 is that the thus produced samples are stored in a secure and hermetic manner in the respective, thus produced capsules. The laboratory analyses require the opening of the thus closed capsules, which is tedious. It is actually necessary to resort to the application of a significant force or to the use of specific equipment, which makes the entire procedure difficult and long.

The drawback of the device of the patent EP 1372379 is that the sample that is produced, even though it can be transported to the laboratory for analysis, is difficult to store and to preserve. Consequently, the laboratory studies have to be carried out over a time interval of several hours to several days after the sampling so as to ensure that the sample is not, at least partially, degraded.

Thus, the object of this invention is to provide a device for sampling biological tissue that is associated with an ear tag that authorizes easy access to the sample that is obtained, which at the same time and despite this easy access makes it possible to store the sample over long periods of time, i.e., from several months to several years. This invention also makes it possible to use the sampling tool with a closed-type animal identification tag, the only type of identification accepted today in most countries using official identification systems.

The inventors had the surprise of discovering that by attaching a tank that is filled with a preservative to one tip of a hollow needle, such as a biopsy needle, it was possible to design a system that can be used to obtain a biological sample during the placing of an ear tag and that this system made possible both instantaneous and easy accessibility to the sample and a long preservation period of the latter. In a practical manner, a dose of a preservative that is intended for the treatment of the sample is enclosed in a tank, one of whose walls is designed to be broken or pierced by the tip of the hollow needle that is adjacent to it, ensuring that the interior of the tank is connected to the cavity of the hollow needle. The preservative then comes into contact with the sample that is taken, at the sharp-edged tip of the hollow needle. The region of the wall of the tank that is designed to be broken or pierced is called a partition here. By a piercing action of this partition, the preservative can exert its action of preservation on the sample that is found in the cavity of the hollow needle. The tip of the hollow needle that contains the sample can be placed in a cup or under a cover that can, at the same time, isolate the tip of the needle in a reversible manner. By so doing, the sample is preserved and during the withdrawal of the cover, the sample is always accessible in the cavity of the needle. It is then possible to expose it to other reagents by simply plunging the needle into the latter or by putting the sample into a suitable laboratory container.

In a preferred embodiment, the device for sampling biological tissue is configured so as to be able to be mounted on a laboratory pipette, such as an Eppendorf pipette, in the form of a cover that contains the distal tip of the needle, i.e., the second tip, and the sample that is found inside.

The samples that are obtained using the device for sampling biological tissue according to this invention can be analyzed easily because they are not enclosed in a capsule that is difficult to open. They can also be preserved for a period of 6 months to 3 years by thus making it possible to determine the biochemical/biological parameters of the samples of biological tissue and the identification of the corresponding animal even after a long period of time.

More specifically, the objectives of this invention are attained using a device for sampling biological tissue that comprises:

A tank that can contain a chemical product for treating a sample of biological tissue, A hollow needle that has a cavity that ends in a first opening at a first tip and in a second opening at a second tip, whereby said hollow needle also has a cutting edge at said second tip that is able to cut out the biological tissue for the purpose of creating a sample that is received in said cavity when the sampling device is pushed into the biological tissue, An attachment part of said hollow needle, formed integral with the tank, whereby said attachment part has a channel that emerges from the base of the tank and ends in an orifice, whereby said channel has dimensions that can hold the proximal part of said hollow needle that carries the first tip, and in that said base of said tank comprises a partition that can be pierced by said first tip of said hollow needle when the sampling device is pushed into the biological tissue.

In a preferred embodiment, said partition comprises a zone of reduced thickness relative to the thickness of the adjacent wall that surrounds said partition or adopts a relief that imparts the least resistance to the pressure, for example using perforations or a groove or a location that will be broken by the first tip of the hollow needle. It is well understood that the zone of less resistance can be obtained by different means known to one skilled in the art (the plasturgist if the device is made of plastic material). A pressure resistance level that is quite low will be sought so that the partition breaks directly at the base of the needle and the neighboring wall of the tank is not damaged. Too low a resistance that would lead the partition to break with less support will be avoided, however, and in particular when the hollow needle can no longer penetrate the tissues that it is to cut for taking a sample.

In a preferred embodiment of the invention, the channel of the attachment part has an inside diameter that is adapted to an outside diameter of the proximal part of the hollow needle, such that said proximal part is engaged by friction in said channel and such that when the sampling device is pushed into the biological tissue, it moves toward the tank by piercing the partition using its first tip.

In a variant embodiment, the tank that comprises the wall and the attachment part are made of plastic, for example by molding. The attachment part and the tank can be made integral so that the attachment part is integrated in the tank by extending the wall. They can also be produced separately, in which case in the device according to the invention, the attachment part is separate from said tank and is connected to the latter by a means of assembly in a second stage. In an alternative embodiment, the attachment part is cast with the tank on the hollow needle.

Preferably, in the device according to the invention, the material of the hollow needle is selected such that it does not alter the biological sample. It can be made of metal or a composite material. Preferably, a metal needle is used.

In a variant embodiment, said hollow needle has a longitudinal shaft that extends between the first and second tips and that is perpendicular to the piercable partition of the tank.

Preferably, the hollow needle is kept perpendicular to said partition of the tank by means of the central channel of said attachment part.

In an advantageous variant embodiment, said tank has an opening that makes it possible to fill it with a chemical product.

According to a preferred embodiment, said tank contains a chemical product for treating a sample of biological tissue, preferably a preservative that can preserve a sample of biological tissue.

Preferably, the preservative is selected from the group that comprises drying agents, enzyme inhibitors, and substances that can prevent the development of bacterial organisms. A drying agent can be, for example, silica gel, calcium sulfate, magnesium oxide, or pyrophosphates. Among the enzyme inhibitors, the DNA-degrading enzyme inhibitors are preferred. Preferably, a substance or a mixture of substances having an action that limits the development of bacterial organisms is placed in the tank.

According to an advantageous characteristic of the device according to the invention, the opening of the tank is closed by a sealed metal sheet. The device according to the invention therefore preferably comes, in its ready-to-use form, with its tank that is filled in advance with a selected chemical product and sealed by a protective cap. For example, said tank that contains a preservative has its opening sealed by an aluminum sheet.

According to an advantageous characteristic of this invention, on its outside part, the tank comprises a collar that allows the use of the sampling device on the male part of an ear tag for tagging animals, whereby said collar has dimensions that make it possible for it to engage in one of the jaws of a pair of pliers used for placing such tags.

In an embodiment of the device for sampling biological tissue according to the invention, said device has a first means of identification.

In a preferred variant of this invention, in the device for sampling biological tissue, the wall of the tank comprises means of association with a cap-shaped cover. For example, the tank can have at its base a part that is sized to be engaged in a cap-shaped cover. In an improved version, said base part is an outside part of said tank. Thus, the device for sampling biological tissue according to the invention is preferably equipped with means of association placed on the outside face at the base of the tank.

Advantageously, the base of the tank that carries the means of association with the cap-shaped cover is extended integral with the attachment part of the hollow needle.

In a particular embodiment of the device for sampling biological tissue according to the invention, the means of association of the tank with a cap-shaped cover have a collar that can hold said cap-shaped cover so that the latter covers the distal part of the hollow needle that optionally contains a sample of biological tissue.

In other words, the base of the tank has a flange that is engaged in the cap-shaped cover when said cover is mounted on said base so that the second tip of the hollow needle, and optionally the sample of biological tissue that is found in the cavity of the needle, is protected by the cap-shaped cover.

Advantageously, the cap-shaped cover is provided with the other elements of the sampling device. This is why a device for sampling biological tissue as described above, which also comprises a cap-shaped cover that is mounted on the flange of said device for sampling biological tissue, is also the object of this invention.

According to a particular embodiment of the device for sampling biological tissue according to the invention, the cap-shaped cover comprises a support of the first means of identification, whereby said means of identification extends from said sampling device.

In a preferred embodiment of the device according to the invention, the cap-shaped cover is made of a transparent material that makes it possible to observe the biological sampling.

Another object of this invention is an ear tag for tagging animals that comprises:

i) A female part, and
ii) A male part that comprises a rod that is equipped with a distal point that has a shoulder that allows the locking of said male part in said female part, whereby said rod is pierced by an axial channel in its entire length, and said male part comprises a device for sampling biological tissue as described above.

In an advantageous embodiment of the ear tag according to the invention, the hollow needle of said device for sampling biological tissue is housed in the axial channel of the rod, whereby the latter has a length such that the cutting edge of the second tip of said hollow needle goes beyond the point of said rod so as to cut out a sample of biological tissue when the male part is pushed through the ear of an animal.

In the ear tag according to the embodiment above, the second tip of the hollow needle goes beyond the point of the rod by a length that is at least equal to the thickness of the partition. Thus, after having penetrated the tissue and having sampled a fraction thereof, the needle slides into the male rod until it is totally housed in said rod, whereby the movement should bring the first tip of the needle through the thin partition up to the tank. This movement should therefore be adequate for shifting the needle up to the interior of the tank, without passing through it entirely, quite obviously.

According to an advantageous characteristic, the ear tag according to the invention also comprises at least one of the following elements:

A second means of identification that is carried by a plate that is combined with the rod of the male part,
A third means of identification that is carried by the female part, ensuring that at least one of the second or third means of identification is found in said ear tag.

It is well understood that the male part that comprises the sampling device as described above is the object of this invention as well as a constituent element of the ear tag per se.

Figure 2:
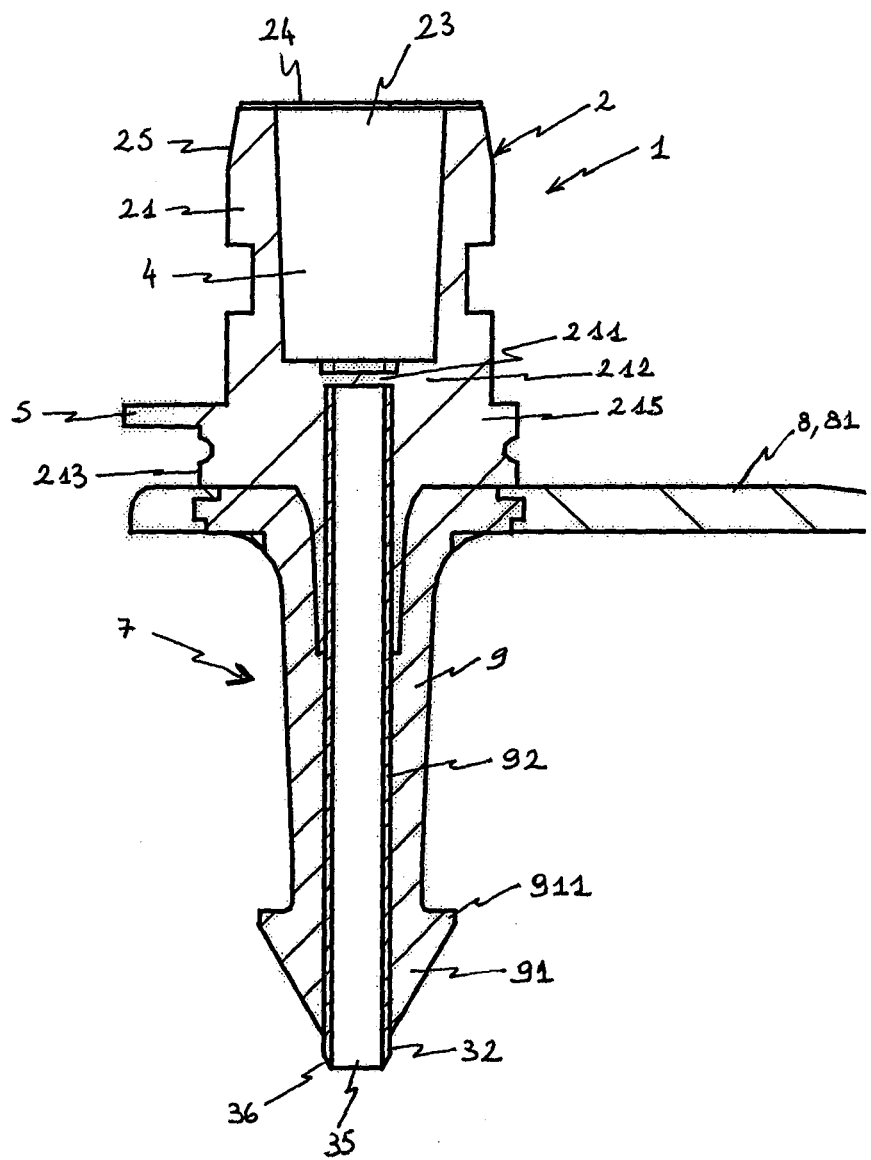
Figure 3:
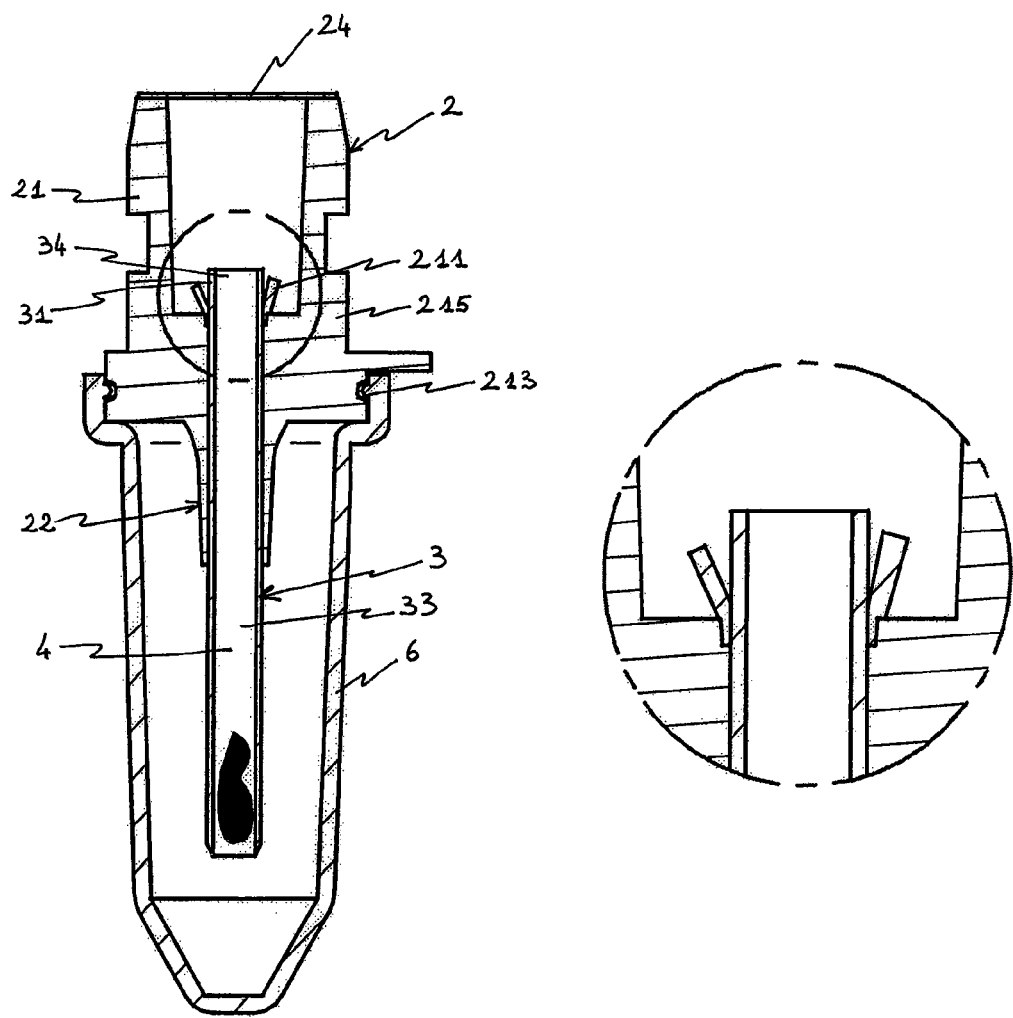

The invention will be better understood based on the embodiment below, illustrated by the figures in which:

FIG. 1 is a longitudinal cutaway view of a device for sampling biological tissue according to this invention, FIG. 2 is a cutaway view of the same device for sampling biological tissue, inserted into the male part of an ear tag, FIG. 3: a cutaway view of the same device, after sampling of biological tissue and combination with a cap-shaped protective cover.

The device for sampling biological tissue 1, as shown in FIG. 1, comprises the tank 2 that contains a preservative 4 for preserving a biological tissue. The tank 2 has the wall 21 that comprises the lateral wall and the base 215. It is equipped with the opening 23 that is closed by the sheet 24. The opening 23 for filling the tank 2 is located here opposite the base 215. After having finished the filling operation, the tank is closed by sealing the sheet 24. Preferably, this sheet will be made of plastic or metal or a combination of the two.

The hollow needle 3, whose first tip 21 is adjacent to the tank 2, and separated from it by the thin partition 211, is held by the cone-shaped attachment part 22. This attachment part 22 has the interior channel 221 that extends from the partition 211 of the tank 2 up to the orifice 35 of the opposite tip 32 (second tip). The needle 3 can move along its longitudinal axis in the channel 221, and if pressure is exerted on the second tip 32 of the needle 3, which is distal relative to the tank 2, the needle 3 moves toward the tank 2. If the thus exerted pressure is significant enough, the needle 3 passes through the partition 211 of the tank 2 with its first tip 31, thus piercing the tank 2 and connecting the inside volume of the hollow needle 3 and the tank 2.

Before taking the sample, the hollow needle 3 is held in a position that is perpendicular to the tank 2 and its first tip 31 close to the tank 2 by means of the attachment part 22 that forms an integral part here of the tank 2. The tank that includes the lateral wall and the base 215 as well as the attachment part 22 are made of plastic material.

The channel 33 of the attachment part 22 is sized to that it receives the hollow needle 3 by friction. This means that to move the hollow needle 3 into the channel 22, it is necessary to exert a certain pressure, such as the pressure that is exerted when the male part of an ear tag is pushed into an animal's ear. This action is sufficient to push the needle 3 a short distance back into the channel 221 and to pierce the partition 211 of the tank 2 that contains the preservative 4, and at the same time to push the cutting edge 36 of the tip 32 of the needle 3 into the ear tissue of the animal so that a small tissue cylinder is cut out and is housed in the opening 35 inside the hollow needle 3.

The hollow needle 3 can be made of metal, hard plastic or any other material that is known to one skilled in the art, since this material is able to withstand the pressures that are usually exerted when an ear tag is placed on an animal and/or when a sample is taken.

The device 1 for sampling biological tissue is advantageously used in combination with the male part 7 of an ear tag 1 as shown in FIG. 2. The male part 7 has the plate 8, the rod 9 that is integral with the plate 8, ending in the distal point 91 that has a shoulder 911 that makes possible the locking of the male part 7 inside a female part of the tag (not shown). The axial channel 92 that extends from the plate 8 to the distal point 91 and that is used to receive the needle 3 of the device 1 for sampling biological tissue is found in the rod 9. The length of the rod 9 has been studied so that the second tip 32 of the hollow needle 3, once the latter is inserted entirely into the rod 9, goes beyond the rod 9, i.e., so that the cutting edge 36 of the tip 32 is free and can cut through the tissue by thus allowing a sample of biological tissue to be taken when the point 91 of the male part 7, including the device 1 for sampling biological tissue, is pushed through the animal's ear into the female part of the tag. The device 1 for sampling biological tissue according to this invention also has the means of identification 5 that carries the information relative to the identity of the animal that is thus tagged and sampled. The identification means 5 of the device 1 for sampling biological tissue according to this invention can be, for example, a visual means or a transponder with an electronic number. If the male part 7 or the female part also has an identification means, these second and third means 81, 111 can be visual or can be transponders that carry information.

FIG. 2 shows that the base 215 of the tank 2 is in contact with the plate 8 of the male part 7 of the tag, when the hollow needle 3 is fully inserted into the rod 9 of said male part. In addition on its outside part, the tank 2 of the sampling device 1 has the collar 25 that makes it possible to mount a unit that consists of the sampling device 1 and the male part 7 on the jaw of a standard pair of pliers.

In addition, the base 215 of the tank 2 has a cap association portion 213 with the flange 214 that can be engaged in the cap-shaped cover 6 as shown in FIG. 3. In certain embodiments, the collar 25 above that is described can be part of the flange 214 or can be the same part as said 14 flange. In other variant embodiments, the collar 25 and the flange 214 are separate. The dimensions of the flange 214 are calculated so that it can be engaged in a cap-shaped cover 6 that, in one preferred variant, is a standard laboratory item, like an Eppendorf pipette. When a cover of this type is mounted on the base 215 of the tank 2, the tip 32 of the needle 3 that contains the sample is found in said cap-shaped cover and can then be subjected to chemical reactions or be placed in a laboratory centrifuge, such as, for example, a portable centrifuge for Eppendorf pipettes.

A device 1 for sampling biological tissue that is equipped with a cap-shaped cover 6 as it is after a sample is obtained is shown in FIG. 3. The means of identification 5 attached to the device 1 for sampling biological tissue makes possible the identification of the sample in the hollow needle 3. The cut-away view of FIG. 3 shows that the needle 3 has been pushed into the tank 2 by piercing and by passing through the partition 211.

The invention claimed is:

1. A device for sampling biological tissue, comprising:
   a tank containing a chemical product for treating a sample of biological tissue,
   the tank comprising a tank wall defining i) a lateral wall, ii) an adjoining base comprising a partition, iii) an opening located opposite the base and configured for filing the tank, and iv) an attachment part adjoining the base and ending with an orifice;
   a hollow needle with a continuous cavity that ends in a first opening at a first tip and in a second opening at a second tip,
   the first and second openings being in fluid communication with each other via the cavity,
   the first tip being held within an interior channel of the attachment part so that the needle extends out from the orifice,
   the needle, under pressure exerted on the second tip, being movable along a longitudinal axis of the interior channel of the attachment part so that said first tip moves towards the partition,
   wherein said hollow needle further comprises a cutting edge at said second tip configured to cut out the biological tissue to create a sample received in said cavity when the cutting edge at said second tip is pushed into the biological tissue,
   wherein said channel has dimensions that hold a proximal part of said hollow needle that carries the first tip, and
   wherein said partition is pierced by said first tip of said hollow needle after the sampling device is pushed into the biological tissue from the biological tissue exerting pressure on the second tip sufficient to move the needle along the longitudinal axis of the interior channel of the attachment part and so that said first tip moves towards and pierces the partition.

2. The device for sampling biological tissue according to claim 1, wherein the partition is defined by a zone of locally reduced thickness partition within the base that imparts less resistance to pressure.

3. The device for sampling biological tissue according to claim 1, wherein the channel has an inside diameter that is adapted to an outside diameter of the proximal part of the hollow needle, such that said proximal part is engaged by friction in said channel and such that when the sampling device is pushed into the biological tissue, the sampling device moves toward the tank.

4. The device for sampling biological tissue according to claim 1, wherein the lateral wall and the attachment part are made of plastic.

5. The device for sampling biological tissue according to claim 1, wherein material of the hollow needle does not alter the biological sample.

6. The device for sampling biological tissue according to claim 1, wherein the hollow needle has a longitudinal shaft that extends between the first and second tips and that is perpendicular to the partition of the tank.

7. The device for sampling biological tissue according to claim 1, wherein the hollow needle is kept perpendicular to the partition of the tank by the channel of the attachment part.

8. The device for sampling biological tissue according to claim 1, wherein the opening is configure for a chemical product passing through the opening to fill the tank.

9. The device for sampling biological tissue according to claim 1, wherein the chemical product for treatment of a sample of biological tissue is a biological tissue preservative.

10. The device for sampling biological tissue according to claim 9, wherein the preservative is selected from a group that comprises drying agents, enzyme inhibitors, and substances that prevent development of bacterial organisms.

11. The device for sampling biological tissue according to claim 1, wherein the opening of the tank is closed by a sealed metal sheet.

12. The device for sampling biological tissue according to claim 1,
   wherein an outside part of the tank comprises a collar that allows the use of said sampling device on a male part of an ear tag for tagging animals, and
   wherein said collar is dimensioned to engage in one jaw of a pair of jaws of a pair of jaws of pliers used for placing tags.

13. The device for sampling biological tissue according to claim 1, wherein said device for sampling biological tissue has a first identification means.

14. The device for sampling biological tissue according to claim 1, wherein the tank wall comprises a cap association portion engaging with a cap-shaped cover.

15. The device for sampling biological tissue according to claim 14, wherein the cap association portion is placed on an outside face at the base of the tank.

16. The device for sampling biological tissue according to claim 15, wherein the base of the tank that carries the cap association portion with the cap-shaped cover is extended integral with the attachment part of the hollow needle.

17. The device for sampling biological tissue according to claim 14, wherein the cap association portion has a flange that in engagement with the cap-shaped cover holds said cap-shaped cover so that the cap-shaped cover covers a distal part of the hollow needle that upon use contains a biological tissue sample.

18. The device for sampling biological tissue according to claim 14, further comprising a cap-shaped cover that is mounted on a flange of said device for sampling biological tissue.

19. The device for sampling biological tissue according to claim 18,
   wherein the cap-shaped cover comprises a support of a first identification means, and
   wherein said first identification means extends from said sampling device.

20. The device for sampling biological tissue according to claim 18, wherein the cap-shaped cover is made of a transparent material for observation of the biological sampling during use.

21. An ear tag for tagging animals that comprises (i) a female part, and ii) a male part that comprises a rod that is equipped with a distal point that has a shoulder that allows a locking of said male part in said female part, wherein along an entire length said rod is pierced by an axial channel, and said male part comprises a device for sampling biological tissue according to claim 1.

22. The ear tag according to claim 21, wherein the hollow needle of said device for sampling biological tissue is housed in the axial channel of the rod, wherein the rod has a length such that the cutting edge of the second tip of said hollow needle goes beyond the distal point of said rod so as to cut out a sample of biological tissue when the male part is pushed through the ear of an animal.

23. The ear tag according to claim 21, wherein the second tip of the hollow needle goes beyond the distal point of the rod by a length that is at least equal to a thickness of the partition.

24. The ear tag according to claim 21, further comprising at least one of the following elements:
- a second means of identification that is carried by a plate that is combined with the rod,
- a third means of identification that is carried by the female part,
- ensuring that at least one of the second or third means of identification is found in said ear tag.

\* \* \* \* \*